United States Patent
Cross, Jr.

(10) Patent No.: US 9,272,965 B2
(45) Date of Patent: Mar. 1, 2016

(54) PROCESS FOR THE CONVERSION OF ALCOHOLS TO OLEFINS

(75) Inventor: William M. Cross, Jr., Kemah, TX (US)

(73) Assignee: Catalytic Distillation Technologies, The Woodlands, TX (US)

(*) Notice: Subject to any disclaimer, the term of this patent is extended or adjusted under 35 U.S.C. 154(b) by 1194 days.

(21) Appl. No.: 12/906,426

(22) Filed: Oct. 18, 2010

(65) Prior Publication Data
US 2011/0152592 A1 Jun. 23, 2011

Related U.S. Application Data

(60) Provisional application No. 61/288,886, filed on Dec. 22, 2009.

(51) Int. Cl.
*C07C 1/213* (2006.01)
*C07C 11/02* (2006.01)

(52) U.S. Cl.
CPC ............ *C07C 11/02* (2013.01); *C07C 1/213* (2013.01)

(58) Field of Classification Search
USPC ......... 585/638, 639, 640, 641, 642, 314, 324, 585/330
See application file for complete search history.

(56) References Cited

U.S. PATENT DOCUMENTS

| | | | | |
|---|---|---|---|---|
| 2,286,407 A * | 6/1942 | Halbig | ............... | 562/609 |
| 2,304,872 A * | 12/1942 | Bryant et al. | ............... | 562/607 |
| 2,366,007 A | 12/1944 | D'Alelio | | |
| 3,068,305 A * | 12/1962 | Heisler et al. | ............... | 585/639 |
| 3,409,698 A * | 11/1968 | Illingworth et al. | ......... | 585/639 |
| 3,931,349 A | 1/1976 | Kuo | | |
| 4,443,559 A | 4/1984 | Smith, Jr. | | |
| 4,620,050 A * | 10/1986 | Cognion et al. | ............ | 585/640 |
| 4,724,049 A | 2/1988 | Berg et al. | | |
| 5,057,468 A | 10/1991 | Adams | | |
| 5,218,052 A | 6/1993 | Cohen et al. | | |
| 5,262,012 A | 11/1993 | Smith, Jr. | | |
| 5,266,546 A | 11/1993 | Hearn | | |
| 5,348,710 A | 9/1994 | Johnson et al. | | |
| 5,510,555 A | 4/1996 | Brunelli et al. | | |
| 5,723,698 A * | 3/1998 | Dai et al. | ............... | 568/913 |
| 5,730,843 A | 3/1998 | Groten et al. | | |
| 6,136,743 A | 10/2000 | Sugimura et al. | | |
| 6,740,783 B1 | 5/2004 | Jun et al. | | |
| 6,884,914 B2 * | 4/2005 | Mathys et al. | ............... | 585/324 |
| 6,888,013 B2 | 5/2005 | Paparatto et al. | | |

(Continued)

FOREIGN PATENT DOCUMENTS

DE 908247 C 4/1954
EP 0582480 A2 2/1994

OTHER PUBLICATIONS

Notification of Transmittal of the International Search Report and the Written Opinion issued Aug. 18, 2011 in corresponding International application No. PCT/US2010/058488 (10 pages).

*Primary Examiner* — In Suk Bullock
*Assistant Examiner* — Sharon Pregler
(74) *Attorney, Agent, or Firm* — Osha Liang LLP

(57) ABSTRACT

A process for the conversion of an alcohol to an olefin is disclosed. The process may include: contacting at least one C2 to C5 alcohol with an organic acid in the presence of an esterification catalyst to convert at least a portion of the at least one C2 to C5 alcohol and the organic acid to an ester; at least one of catalytically and thermally degrading the ester to form an organic acid and an olefin.

23 Claims, 4 Drawing Sheets

(56) References Cited

U.S. PATENT DOCUMENTS

| | | |
|---|---|---|
| 6,936,742 B2 | 8/2005 | Smith, Jr. |
| 7,198,874 B2 | 4/2007 | Saito et al. |
| 7,220,710 B2 | 5/2007 | Kunz et al. |
| 7,361,692 B2 | 4/2008 | Thetford |
| 7,399,873 B2 | 7/2008 | Souda et al. |
| 2003/0124038 A1* | 7/2003 | Moritz et al. .............. 422/211 |
| 2007/0092957 A1 | 4/2007 | Donaldson et al. |
| 2007/0260077 A1* | 11/2007 | Elliott ....................... 554/174 |
| 2008/0013274 A1 | 1/2008 | Jobs et al. |
| 2008/0015395 A1 | 1/2008 | D'amore et al. |
| 2008/0045754 A1 | 2/2008 | D'Amore et al. |
| 2008/0234523 A1 | 9/2008 | Manzer et al. |
| 2008/0275260 A1* | 11/2008 | Elliott ........................... 554/1 |
| 2009/0030239 A1 | 1/2009 | D'Amore et al. |
| 2009/0099401 A1 | 4/2009 | D'Amore et al. |

\* cited by examiner

US 9,272,965 B2

PROCESS FOR THE CONVERSION OF ALCOHOLS TO OLEFINS

CROSS-REFERENCE TO RELATED APPLICATION

This application, pursuant to 35 U.S.C. §119(e), claims priority to U.S. Provisional Application Ser. No. 61/288,886, filed Dec. 22, 2010. That application is incorporated by reference in its entirety.

FIELD OF THE DISCLOSURE

Embodiments disclosed herein relate generally to a process for the conversion of light alcohols to olefins. In another aspect, embodiments disclosed herein relate to processes for the conversion of C2 to C5 alcohols, including isobutanol and isopentanol, to olefins, such as isobutylene and isoamylenes.

BACKGROUND

Isobutanol can be formed from the fermentation of sugars which can be formed via the breakdown of cellulose. For example, solutions of up to approximately 2% by weight isobutanol in microbial growth have been produced in certain fermentation processes (Fraces Arnold, "The Race for New Biofuels," Engineering & Science, No. 2, 2008). U.S. Patent Application Publication No. 20070092957 describes fermentatively producing isobutanol using recombinant microorganisms.

As microbes are further developed to withstand higher concentrations of isobutanol, it can be envisioned that isobutanol may compete with ethanol as a potential—fuel component or chemical feedstock derived from renewable resources. Unfortunately, there exist concerns regarding direct blending of isobutanol and other higher alcohols into the gasoline pool due to odor and automotive component compatibility issues. For this reason, there is interest in conversion of light alcohols into more typical petrochemical feedstocks for conversion into fuels or other valuable end products.

U.S. Patent Application Publication Nos. 20090099401, 20090030239, 2008013274, 20080045754, 20080015395, 20080234523, and others, each filed by E.I. Dupont de Nemours and Company, Wilmington, Del., are directed to the conversion of bio-derived isobutanol to butenes and isooctenes, among other end products. Each of these processes react isobutanol over a homogeneous or heterogeneous acid catalyst to form the desired reaction product, either a butene or an isooctene (diisobutylene).

Unlike tertiary butanol, which can be readily converted via dehydration into its constituent isobutylene and then into fuel blend components, such as diisobutylene, as disclosed in U.S. Pat. No. 6,936,742, the conversion of other light alcohols often requires higher activity catalysts and more severe process conditions. Significant recycle rates may also be required to result in acceptable conversion levels. Additionally, with bio-derived alcohols, water may be present with the feed, and separation is often difficult due to the components having closer relative volatilities and potential for forming various azeotropes.

Accordingly, there exists a need for processes for the conversion of light alcohols such as isobutanol into useful petrochemical feedstocks.

SUMMARY OF THE CLAIMED EMBODIMENTS

In one aspect, embodiments disclosed herein relate to a process for the conversion of an alcohol to an olefin, the process including: contacting at least one C2 to C5 alcohol with an organic acid in the presence of an esterification catalyst to convert at least a portion of the at least one C2 to C5 alcohol and the organic acid to an ester; at least one of catalytically and thermally degrading the ester to form an organic acid and an olefin.

In another aspect, embodiments disclosed herein relate to a process for the conversion of an alcohol to an olefin, the process including: feeding at least one C2 to C5 alcohol and an organic acid to a first reaction zone containing an esterification catalyst; contacting the at least one C2 to C5 alcohol with the organic acid in the presence of the esterification catalyst to convert at least a portion of the at least one C2 to C5 alcohol and the organic acid to an ester and water; recovering a reactor effluent from the first reaction zone comprising water, ester, any unreacted organic acid, and any unreacted C2 to C5 alcohol; feeding the reactor effluent from the first reaction zone to a catalytic distillation reactor system having at least one reaction zone containing an esterification catalyst; concurrently in the catalytic distillation reactor system: contacting the at least one C2 to C5 alcohol with the organic acid in the presence of the esterification catalyst to convert at least a portion of the at least one C2 to C5 alcohol and the organic acid to an ester and water; separating the water, ester, any unreacted organic acid, and any unreacted C2 to C5 alcohol; recovering a first fraction from the catalytic distillation reactor system comprising water; recovering a second fraction from the catalytic distillation reactor system comprising the ester; at least one of catalytically and thermally degrading the ester to form a degradation product comprising an organic acid and an olefin; and separating the degradation product to recover a third fraction comprising organic acid and any unreacted ester and a fourth fraction comprising the olefin.

Other aspects and advantages will be apparent from the following description and the appended claims.

DETAILED DESCRIPTION

Figure 1:
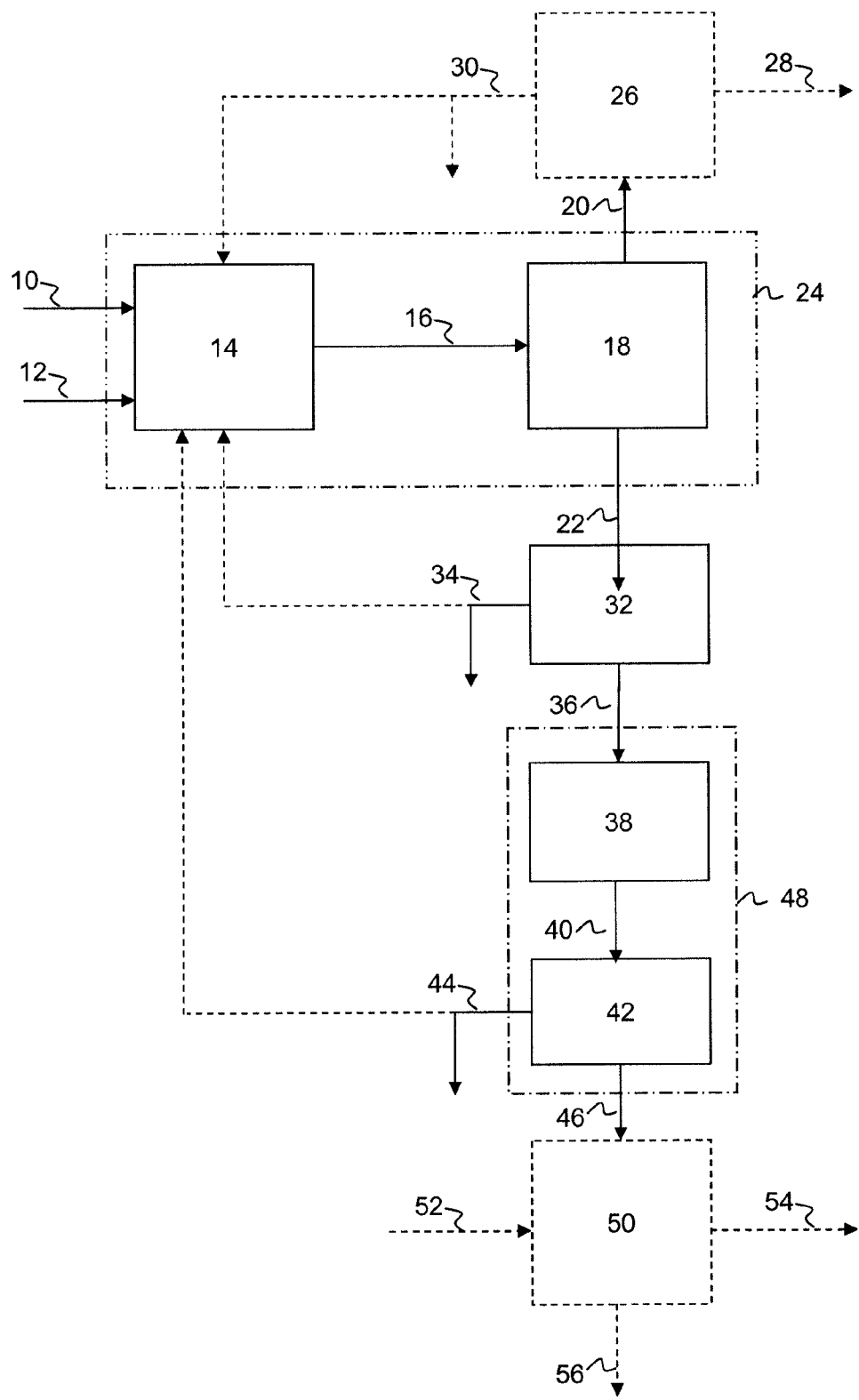
FIG. 1 is a simplified block flow diagram of a process for the conversion of alcohols to olefins according to embodiments disclosed herein.

Within the scope of this application, the expression "catalytic distillation reactor system" denotes an apparatus in which the catalytic reaction and the separation of the products take place at least partially simultaneously. The apparatus may comprise a conventional catalytic distillation column reactor, where the reaction and distillation are concurrently taking place at boiling point conditions, or a distillation column operatively connected with at least one side reactor to which a sidedraw from the distillation column is introduced as a feed and from which a reactor effluent is withdrawn and returned to the distillation column, where the side reactor may be operated as a liquid phase reactor, a vapor phase reactor, or a boiling point reactor. While both catalytic distillation reactor systems described may be preferred over conventional liquid phase reaction followed by separations, a catalytic distillation column reactor may have the advantages of decreased piece count, reduced capital cost, increased catalyst productivity per pound of catalyst, efficient heat removal (heat of reaction may be absorbed into the heat of vaporization of the mixture), and a potential for shifting equilibrium. Divided wall distillation columns, where at least one section of the divided wall column contains a catalytic distillation structure, may also be used, and are considered "catalytic distillation reactor systems" herein.

Processes disclosed herein may include any number of reactors, including catalytic distillation reactor systems, both up-flow and down-flow. Use of catalytic distillation reactor systems may prevent foulants and heavy catalyst poisons in the feed from contacting the catalyst. In addition, clean reflux may continuously wash the catalyst zone. These factors combine to provide a long catalyst life. The heat of reaction evaporates liquid and the resulting vapor is condensed in the overhead condenser to provide additional reflux.

Other reactors useful in embodiments disclosed herein may include traditional fixed bed reactors, boiling point reactors, and pulsed flow reactors, where the reactant flow and product flow may be co-current or counter-current. Boiling point and pulsed flow reactors may also provide for a continuous washing of the catalyst in addition to capturing at least a portion of the heat of reaction through evaporation, allowing for an improved reactor temperature profile as compared to conventional fixed bed reactors.

In one aspect, embodiments herein relate to a process for the conversion of light alcohols to olefins. In another aspect, embodiments disclosed herein relate to processes for the conversion of light (C2 to C10) alcohols, such as isobutanol and isopentanol, to olefins, such as isobutylene and isoamylenes.

Conversion of light alcohols to olefins according to embodiments disclosed herein may proceed via esterification of the alcohol with an organic acid to form an ester, followed by degradation of the ester to form an organic acid and an olefin. For example, isobutanol may initially be reacted with acetic acid to form isobutyl acetate, a C6 ester. The isobutyl acetate may subsequently be thermally or catalytically degraded (cracked) to produce acetic acid and isobutylene.

Producing olefins from light alcohols in this manner may reduce or eliminate the need for high activity catalysts, severe processing conditions (relatively high temperatures and/or pressures), and high recycle rates, as are typically required for dehydration of alcohols such as isobutanol and isopentanol. As such, processes disclosed herein provide for the conversion of various alcohols and bio-alcohols, including mixtures of bio-alcohols, to useful petrochemical compounds.

In general, processes for the conversion of an alcohol to an olefin according to embodiments disclosed herein may include: contacting at least one of a C2 to C5 alcohol with an organic acid in the presence of an esterification catalyst to form an ester; and catalytically or thermally degrading the ester to form an organic acid and an olefin. Intermediate to these reaction steps may be one or more separation stage for the separation of unreacted feed components and byproducts from the target reaction product. The specific process steps may thus depend upon the separation processes used, such as distillation, extractive distillation, and the like, the relative boiling points of the reactants and products, and other factors as may be apparent to one skilled in the art.

Referring now to FIG. 1, a simplified block flow diagram of processes for the conversion of an alcohol to an olefin according to embodiments disclosed herein is illustrated. One or more process streams 10, 12 may be used to introduce an alcohol, such as an alcohol recovered from a fermentation process, and an organic acid to a reaction zone 14. In reaction zone 14, the alcohol and organic acid may be contacted in the presence of an esterification catalyst to form a reaction product comprising esters, water, any unreacted organic acid and any unreacted alcohol.

The esterification reaction may be conducted at various temperatures and pressures appropriate for the specific alcohols and organic acids, as well as the reactor type. For example, fixed bed reactors may be operated as a vapor-phase reactor, a liquid phase reactor, or a mixed vapor-liquid reactor, where the operating temperatures and pressures are selected to maintain the desired phase(s). Catalytic distillation reactor systems are also operated at temperatures and pressures to concurrently maintain the desired reaction zone temperature and perform the desired separations. In some embodiments, the esterification reaction zone may be at temperatures may be in the range from about 85° F. (29° C.) to 570° F. (299° C.) and pressures in the range from about 7 psia to about 620 psia (0.5 bar to 43 bar); from about 100° F. (37° C.) to about 400° F. (204° C.) in other embodiments; from about 130° F. (54° C.) to about 300° F. (149° C.) in other embodiments; and from about 100° F. (37° C.) to about 230° F. (110° C.) in yet other embodiments.

The resulting reaction product 16 may then be separated in a separation zone 18 to recover an aqueous fraction 20, comprising water, and a first ester fraction 22, comprising ester. In some embodiments, reaction zone 14 and separation zone 18 may be at least partially combined in a reaction/separation zone 24 including at least one catalytic distillation reactor system (not shown), as will be further described below. The primary separation targeted in separation zone 18 (or reaction/separation zone 24) is between water and the product ester. Secondarily, any unreacted alcohol and any unreacted organic acid may be separated into the aqueous fraction and the first ester fraction based upon relative boiling points.

Aqueous fraction 20 may thus include water and one of unreacted alcohol and unreacted organic acid. Depending upon the water content, aqueous fraction 20, or a portion thereof may be directly recycled to reaction zone 14 to convert additional alcohol (or organic acid) to ester. If desired, aqueous fraction 20 may be further separated in separation zone 26 to recover a water fraction 28 and an alcohol fraction 30 (or an organic acid fraction 30), a portion or all of which may be recycled to reaction zone 14 and/or used as reflux for separation zone 18 or combined reaction/separation zone 24.

The ester fraction 22 may include ester and one of unreacted alcohol and unreacted organic acid (i.e., the unreacted component not contained in the aqueous fraction), and may then be fed to separation zone 32, which may include one or more separation steps. In separation zone 32, the ester may be separated from the unreacted organic acid (or the unreacted alcohol), where the unreacted organic acid (or unreacted alcohol) may be recovered via flow line 34 and a second ester fraction may be recovered via flow line 36.

The second ester fraction may then be fed via flow line 36 to reaction zone 38. In some embodiments, the ester may be thermally decomposed in reaction zone 38 to form a decomposition reaction product comprising olefin and organic acid. In other embodiments, the second ester fraction may additionally or alternatively be contacted with a decomposition catalyst in reaction zone 38 to form a decomposition reaction product comprising olefin and organic acid. The decomposition reaction product 40 may then be separated in separation zone 42 to recover an organic acid fraction 44 and an olefin fraction 46.

In some embodiments, reaction zone 38 and separation zone 42 may be at least partially combined in a catalytic or non-catalytic reaction/separation zone 48, which may include at least one catalytic or non-catalytic distillation reactor system (not shown), as will be further described below. For example, reboil temperatures within a distillation column may be sufficiently elevated to decompose the ester to the desired products. In other embodiments, a decomposition catalyst may be located at an appropriate elevation within a distillation column to result in the desired decomposition products, where reboil temperatures may optionally be elevated to additionally contribute to the desired decomposition reaction.

The decomposition reaction may be conducted at various temperatures and pressures appropriate for the specific ester, the reactor type, and reaction type, catalytic or non-catalytic. In some embodiments, decomposition reaction zone temperatures may be in the range from about 100° F. (37° C.) to about 820° F. (438° C.) and at pressures in the range from about 7 psia to about 1050 psia (0.5 bar to about 72 bar). Temperatures less than the acid degradation temperatures should be used. In other embodiments, temperatures in the range from about 200° F. (93° C.) to below 820° F. (438° C.) may be used; from about 200° F. (93° C.) to about 650° F. (343° C.) in other embodiments. When catalytically degraded, temperatures in the range from about 200° F. (93° C.) to about 500° F. (260° C.) may be used.

The organic acid fractions (44 and one of 30 and 34) recovered from separation zones 42 and one of 26 and 32 may be totally or partially recycled to reaction zone 14. The olefin fraction 46 recovered from separation zone 42 may contain trace amounts of organic acid. If desired or necessary prior to further processing or use of the olefin, olefin fraction 46 may be fed to water wash system 50 for contact with water 52, partitioning at least a portion or all of the organic acid, as well as any alcohols entering the decomposition step, to the recovered water phase 54 and resulting in an olefin product 56 having essentially no organic acid or other impurities. The resulting olefin or mixture of olefins may then be separated, if necessary, to recover olefins of discrete carbon number (e.g., separation of ethylene from isobutylene).

Olefin fraction(s) produced according to embodiments of the processes disclosed herein may have a purity of 98 wt. % or higher. In other embodiments, olefin fractions produced may have an olefin content of 98.5 wt. % or greater; an olefin content of 99 wt. % or greater in other embodiments; an olefin content of 99.5 wt. % or greater in other embodiments; an olefin content of 99.8 wt. % or greater in other embodiments; and an olefin content of 99.9 wt. % or greater in yet other embodiments. Due to the high purity of the olefins recovered, the olefins produced and recovered according to embodiments disclosed herein may be further processed to form any number of products, including polymers and various specialty chemicals.

As described above, embodiments disclosed herein may be used to convert various alcohols to olefins using organic acids, esterification catalysts, and, optionally, decomposition catalysts. Alcohol feedstocks useful in embodiments disclosed herein may include $C_2$ to $C_6$ primary, secondary, and tertiary alcohols. Examples of alcohols useful in embodiments disclosed herein include ethanol, n-propanol (1-propanol), isopropanol, n-butanol (1-butanol), 2-butanol, isobutanol, t-butanol, and the various pentanol isomers, among others. In some embodiments, the alcohol may comprise, consist essentially of, or consist of isobutanol. In other embodiments, isobutanol may be used in combination with one or more of the $C_{2+}$ alcohols.

In some embodiments, the alcohols useful in embodiments disclosed herein may include bio-alcohols, such as bio-derived ethanol or bio-derived isobutanol, for example. Bio-alcohols are a feed material that may be derived from renewable resources, such as corn, corn stalks, corn cobs, lignocellulose, sugarcane, sugar beets, and wheat, among others. While direct blending of the alcohol into gasoline may be performed by simple mixing, the odor, vapor pressure, or material compatibility of the gasoline may be negatively affected due to the alcohol. Use of bio-alcohols according to embodiments disclosed herein may provide an alternative method to incorporate a renewable resource, bio-alcohol, as a gasoline feed stock, without the undesirable effects.

In some embodiments, the alcohol or mixture of alcohols may be derived from a renewable resource via a fermentation process, such as described in U.S. Patent Application Publication No. 20070092957, which is incorporated herein by reference to the extent not contradictory to embodiments disclosed herein. Further, the resulting fermentation product may be worked up to achieve a wet or dry alcohol, such as described in U.S. Patent Application Publication No. 20090030239 and others as mentioned above, each of which is incorporated herein by reference to the extent not contradictory to embodiments disclosed herein.

Fermentation methodology is well known in the art, and can be carried out in a batch-wise, continuous or semi-continuous manner. As is well known to those skilled in the art, the concentration of isobutanol in the fermentation broth produced by any process will depend on the microbial strain and the conditions, such as temperature, growth medium, mixing and substrate, under which the microorganism is grown.

Following fermentation, the fermentation broth from the fermentor can be used in embodiments disclosed herein. In some embodiments, the fermentation broth is subjected to a refining process to produce an aqueous stream comprising an enriched concentration of isobutanol. As used herein, "refining process" refers to a process comprising one unit operation or a series of unit operations that allows for the purification of an impure aqueous stream comprising isobutanol yielding an aqueous stream comprising substantially pure isobutanol. For example, in one embodiment, the refining process yields a stream that comprises at least about 5% water and isobutanol, but is substantially free of ethanol that may have been present in the fermentation broth.

Refining processes typically utilize one or more distillation steps as a means for recovering a fermentation product. It is expected, however, that fermentative processes will produce isobutanol at very low concentrations relative to the concentration of water in the fermentation broth. This can lead to large capital and energy expenditures to recover the isobutanol by distillation alone. As such, other techniques can be used either alone or in combination with distillation as a means of concentrating the dilute isobutanol product. In such processes where separation techniques are integrated with the fermentation step, cells are often removed from the stream to be refined by centrifugation or membrane separation techniques, yielding a clarified fermentation broth. These cells are then returned to the fermentor to improve the productivity of the isobutanol fermentation process. The clarified fermentation broth is then subjected to such techniques as pervaporation, gas stripping, liquid-liquid extraction, perstraction, adsorption, distillation, or combinations thereof. Depending on product mix, these techniques can provide a stream comprising water and isobutanol suitable for use in the processes disclosed herein. If further purification is necessary, the stream can be treated further by distillation to yield an aqueous or dry isobutanol stream.

Esterification of alcohols with an organic acid produces water as a by-product, which is then separated from the desired ester. As such, alcohol feedstocks useful in embodiments disclosed herein may include wet alcohol feedstocks (i.e., admixed with water), or may be dry alcohol feedstocks (i.e., essentially free of water).

In some embodiments, alcohol feedstocks useful in embodiments disclosed herein may contain from 0.1 to 100 wt. % alcohol and from 0 to 99.9 wt. % water. In other embodiments, the alcohol feedstock may contain from 10 to 100 wt. % alcohol; from 25 to 100 wt. % alcohol in other embodiments; and from 50 to 95 wt. % alcohol in yet other embodiments. The amount of water that may be used within the catalytic esterification zone may depend on (1) the reaction equilibrium constant and (2) the strength/activity of the acid catalyst for conversion. For example, as one moves from resin type catalysts to stronger sulfuric or hydrochloric acid concentrations, activity can be maintained at higher water concentrations. Acid resin catalysts will be more susceptible to loss in catalyst activity due as one moves to larger quantities of water at elevated temperatures.

For ethanol, the preferred concentration is the azeotropic ethanol/water composition, approximately 95% wt ethanol, since both the formate and acetate ester equilibrium is very favored and active heterogenous and homogeneous catalysts are readily available. For isobutanol, the water azeotropic composition is 67% wt isobutanol, favoring either (1) increased purity feed prior to the catalytic distillation step, or (2) the addition of an extractive agent for the suppression of the water relative volatility within the catalytic zone so that reaction equilibrium per distillation stage and kinetic activity within each stage can be enhanced.

Examples of organic acids useful in embodiments disclosed herein include acetic acid, formic acid, propionic acid, butyric acid, isobutyric acid, hexanoic acid, 4-methylvaleric acid, heptanoic acid, oleic acid, lactic acid, benzoic acid, succinic acid, and stearic acid. In particular embodiments, the organic acid may include acetic acid, formic acid, succinic acid, and/or lactic acid.

The ratio of alcohol to organic acid may be in the range from about 0.5:1 to about 2:1 in some embodiments; from about 0.8:1 to about 1.25:1 in other embodiments; from about 0.9:1 to about 1.1:1 in other embodiments; and at about 1:1 in yet other embodiments. Use of excess alcohol may be advantageous in some embodiments as high concentrations of the organic acid may affect equipment design, i.e., a need to account for the corrosivity of the organic acid.

Catalysts that may be used in the fixed bed reactors and the distillation column reactor systems for the esterification of isobutanol and the degradation of the resulting ester to isobutylene are generally acidic catalysts. Zeolites and metal substituted cationic resin catalysts may be used for this reaction, but other mildly acidic catalyst may also be used. The specific catalyst or mixtures of catalysts used in the esterification reaction zone and the degradation reaction zone may be the same or different.

Examples of esterification catalysts include Lewis acids, alkali metals, sulfonic acids, etc. Specific examples of Lewis acids include aluminum derivatives, tin derivatives, and titanium derivatives. Examples of alkali metal derivatives are sodium alkoxides, potassium alkoxides, etc. Examples of sulfonic acids include aryl or alkyl sulfonic acids, including benzenesulfonic acid, para-toluenesulfonic acid, dodecyl-benzenesulfonic acid, methanesulfonic acid, ethanesulfonic acid and trifluoromethanesulfonic acid, as well as sulfuric acid, among others.

Examples of solid acids useful as esterification catalysts according to embodiments disclosed herein may include strongly acidic ion exchangers or zeolites, such as activated clay, acid clay, faujasite, X-type zeolite, Y-type zeolite, mordenite, silica—alumina, and acidic ion exchange resins.

Other esterification catalysts that may be used in embodiments disclosed herein may include tin oxalate or other esterification catalysts disclosed in U.S. Pat. No. 7,220,710, tetrabutoxy titanate and dibutyltinoxide, as disclosed in U.S. Pat. No. 7,198,874, zirconium catalyst as described in U.S. Pat. No. 7,399,873, as well as tetra-alkyl titanate, for example tetrabutyl titanate, a zinc salt of an organic acid, such as zinc acetate, a zirconium salt of an aliphatic alcohol, for example zirconiumbutylate, toluene sulphonic acid or a strong acid such as trifluoroacetic acid, as disclosed in U.S. Pat. No. 7,361,692, each of which are incorporated herein by reference to the extent not contradictory to embodiments disclosed herein.

Degradation of the ester may be performed thermally, cracking the ester to form an olefin and an organic acid. In other embodiments, the degradation of the ester may be performed in the presence of one or more acidic catalyst, which may be the same or different than the esterification catalysts.

Other acidic catalysts useful for the esterification and degradation reactions in embodiments disclosed herein may include naturally occurring zeolites have irregular pore size and are not generally considered as equivalent to synthetic zeolites. In some embodiments, however, naturally occurring zeolites are acceptable so long as they are substantially pure. The balance of the present discussion shall be directed to the synthetic zeolites with the understanding that natural zeolites are considered equivalent thereto as indicated above, i.e., in so far as the natural zeolites are the functional equivalents to the synthetic zeolites.

Synthetic zeolites may be prepared in the sodium form, that is, with a sodium cation in close proximity to each aluminum tetrahedron and balancing its charge. A number of principal types of molecular sieves have been reported, such as A, X, Y, L, erionite, omega, beta, and mordenite. The A-type molecular sieves have relatively small pore size. By the term pore size is meant the effective pore size (diameter) rather than the free pore size (diameter). X- and Y-type molecular sieves generally have a larger pore size (approximately 7.4 Å) and differ as to the range of ratio of $Al_2O_3$ to $SiO_2$. Type L and other types listed have still higher ratios of SiO, to $Al_2O_3$, as known in the art.

Zeolite catalysts that may be used in embodiments disclosed herein are the acid form of the zeolite or at least exhibit acidic characteristics. The acid form is commercially available, but also may be prepared by treating the zeolites with acid to exchange Na for hydrogen. Another method to produce the acid form is to treat the zeolite with decomposable cations (generally ammonium ions) to replace Na with the decomposable ions and thereafter to heat the mole sieve to decompose the cation leaving the acid form. Generally the Na form is treated with ammonium hydroxide to remove the Na and thereafter the zeolite is heated to a temperature of about 350° C. to remove the ammonia. The removal of $Na^+$ ions with $NH_4^+$ is more easily carried out than with multivalent ions, as described below, and these catalysts are generally more active, but less stable to heat than the multivalent cation exchange forms. Zeolites, which have had their alkali metal reduced to low levels by partial treatment with $NH_4^+$ and partial multivalent metal cation exchange, may be expected to possess increased activity and increased stability.

Pore size within the crystal lattice may be significant in this reaction. According to one theory of molecular sieve catalytic activity, zeolite catalysis occurs primarily inside the uniform crystal cavities; consequently, zeolitic catalyst activity depends on the number of aluminum atoms in the crystal and thus on the chemical composition of the crystal. Moreover, these catalytic sites are fixed within the rigid structure of the crystal, meaning that access to active sites can be altered by altering the structure of the crystal.

In some embodiments, acidic resin catalysts may also be used. For example, resin catalyst compositions such as sulfonic acid resins which have at least 50% of the sulfonic acid groups neutralized with one or more metal ions of Groups 4-12 of the Periodic Table, the rare earth metals, or mixtures thereof. The balance of the sulfonic acid groups may be neutralized with an alkali metal or alkaline earth metal, ammonium, or mixtures thereof. The sulfonic acid may be attached to any polymeric backbone. In some embodiments, the metal ions may include one or more of Ti, V, Cr, Mn, Fe, Co, Ni, Cu, Zn, Zr, Nb, Mo, Ru, Rh, Pd, Ag, Cd, Ta, W, Re, Pt, Ce, Nd, Sm, and Eu. The metal modified resin catalyst compositions are disclosed in U.S. Pat. Nos. 4,551,567 and 4,629,710, each of which are incorporated herein.

Acid cation exchange resins are well known and have a wide variety of uses. The resins are cation exchangers that contain sulfonic acid groups which may be obtained by polymerization or copolymerization of aromatic vinyl compounds followed by sulfonation. Aromatic vinyl compounds suitable for preparing polymers or copolymers are: styrene, vinyl toluene, vinyl naphthalene, vinyl ethylbenzene, methyl styrene, vinyl chlorobenzene, and vinyl xylene. A large variety of methods may be used for preparing these polymers. For example, polymerization alone or in admixture with other monovinyl compounds, or by crosslinking with polyvinyl compounds, such as divinyl benzene, divinyl toluene, and divinylphenylether, among others. The polymers may be prepared in the presence or absence of solvents or dispersing agents, and various polymerization initiators may be used, e.g., inorganic or organic peroxides, persulfates, etc.

The sulfonic acid group may be introduced into these vinyl aromatic polymers by various known methods; for example, by sulfating the polymers with concentrated sulfuric and chlorosulfonic acid, or by copolymerizing aromatic compounds which contain sulfonic acid groups (see e.g., U.S. Pat. No. 2,366,007). Further sulfonic acid groups may be introduced into the polymers which already contain sulfonic acid groups; for example, by treatment with fuming sulfuric acid, i.e., sulfuric acid which contains sulfur trioxide. The treatment with fuming sulfuric acid is preferably carried out at 0 to 150° C. and the sulfuric acid should contain sufficient sulfur trioxide so that it still contains 10 to 50% free sulfur trioxide after the reaction. The resulting products may contain an average of 1.3 to 1.8 sulfonic acid groups per aromatic nucleus. Particularly, suitable polymers containing sulfonic acid groups are copolymers of aromatic monovinyl compounds with aromatic polyvinyl compounds, particularly, divinyl compounds, in which the polyvinyl benzene content is preferably 1 to 20% by weight of the copolymer (see, for example, DE 908,247).

The ion exchange resin may have a granular size of about 0.25 to 1 mm, although particles from 0.15 mm up to about 2 mm may be used. The finer catalysts provide high surface area, but also result in high pressure drops through the reactor. The macroreticular form of these catalysts have a much larger surface area exposed and undergo limited swelling in a non-aqueous hydrocarbon medium compared to the gelular catalysts.

The metal modified catalyst may be prepared by contacting a macroporous matrix containing a sulfonic acid group with an aqueous solution of metal salts and solutions of alkali metal salts, alkaline earth metal salts, and/or ammonium salts to neutralize the acid groups. An alternative procedure for the preparation of the metal modified cation resin catalyst compositions comprises contacting a sulfonic acid cation exchange resin, e.g., a macroporous matrix of a polyvinyl aromatic compound crosslinked with a divinyl compound and having thereon from about 3 to 5 milli-equivalents of sulfonic acid groups per gram of dry resin, (1) with an aqueous solution of a soluble metal salt as described above, such as Al, Fe, Zn, Cu, Ni, or mixtures thereof, to neutralize at least 50% to less than 100% of the available sulfonic acid groups with metal ions to produce a partially neutralized resin, and (2) thereafter contacting the partially neutralized resin with an aqueous solution containing a soluble compound of an alkali or alkaline earth metal of Groups 1 or 2, of the Periodic Table, or mixture thereof to neutralize the remaining sulfonic acid groups. In the final alkali neutralization step under the alternate procedure, care must be exercised to not contact the partially neutralized resin with a large excess of alkali or alkaline earth metal ions, (a slight excess, up to about 20%, beyond that required to neutralize the residual sulfonic acid groups may be used) since they appear to form double salts or possibly elute the metal ions, which may reduce the activity of the catalyst.

Resin catalyst composition useful herein may be characterized as a solid comprising a macroporous matrix of polyvinyl aromatic compound crosslinked with a divinyl compound and having thereon from about 3 to 5 milli-equivalents of sulfonic acid groups per gram of dry resin, wherein at least 50 percent to less than 100 percent of said sulfonic acid groups are neutralized with a metal ion as described above; in other embodiments, at least 59 percent may be neutralized; and from about 70 percent to about 90 percent neutralized in yet other embodiments. Sulfonic acid groups not neutralized with the metal ion may be neutralized with alkali or alkaline earth metal ions of Group 1 or 2 of the Periodic Table, ammonium ions, or mixtures thereof.

The catalyst may be used in any form, including as a distillation structure or incorporated into a distillation structure, and in some embodiments may be a particulate catalysts enclosed in a porous container, such as cloth, screen wire, or polymeric mesh. The material used to make the container may be inert to the reactants and conditions in the reaction system. Particles of about 0.15 mm size or powders up to about ¼ inch diameter may be disposed in the containers. The container used to hold the catalyst particles may have any configuration, such as pockets, or the container may be a single cylinder, sphere, doughnut, cube, tube, or the like.

Spacing component intimately associated with the catalyst component may be provided to space the various catalyst components away from one another. Thus, the spacing component provides in effect a matrix of substantially open space in which the catalyst components are randomly but substantially evenly distributed. One such structure is that shown in U.S. Pat. No. 5,730,843, incorporated by reference herein. In addition, commonly assigned U.S. Pat. Nos. 4,443,559, 5,057,468, 5,262,012, 5,266,546, and 5,348,710 disclose a variety of catalyst structures for this use and are incorporated by reference herein.

U.S. Pat. No. 6,740,783, incorporated by reference herein, discloses other catalysts that may be useful for the production of isoolefins according to embodiments herein. Disclosed are hydrophobic zeolites serving as a catalyst, such as USY, mordenite, ZSM-type, and Beta zeolites whose hydrogen cations are partially replaced with suitable metal ions, such as Group 1, 2, 11, or 12 metal ions, or ammonium ions. Other useful catalysts for the degradation reaction may be disclosed in U.S. Pat. No. 3,931,349.

Catalysts used in the esterification and degradation reactors in various embodiments disclosed herein may include metal-treated zeolites, preferably acidic, hydrofluoric acid-treated clays, and silica-alumina catalysts, such as a 20% silica-alumina, among the other catalysts described above. Other preferred catalysts may include acidic resin catalysts, metalized resins and silica-alumina catalysts, among the other catalysts described above. Acidic resin catalysts may include, for example AMBERLYST 15 and AMBERLYST 35. Metalized resin catalysts may include such catalysts as zinc-treated AMBERLYST 15 and copper-treated AMBERLYST 35, among others.

Figure 2:
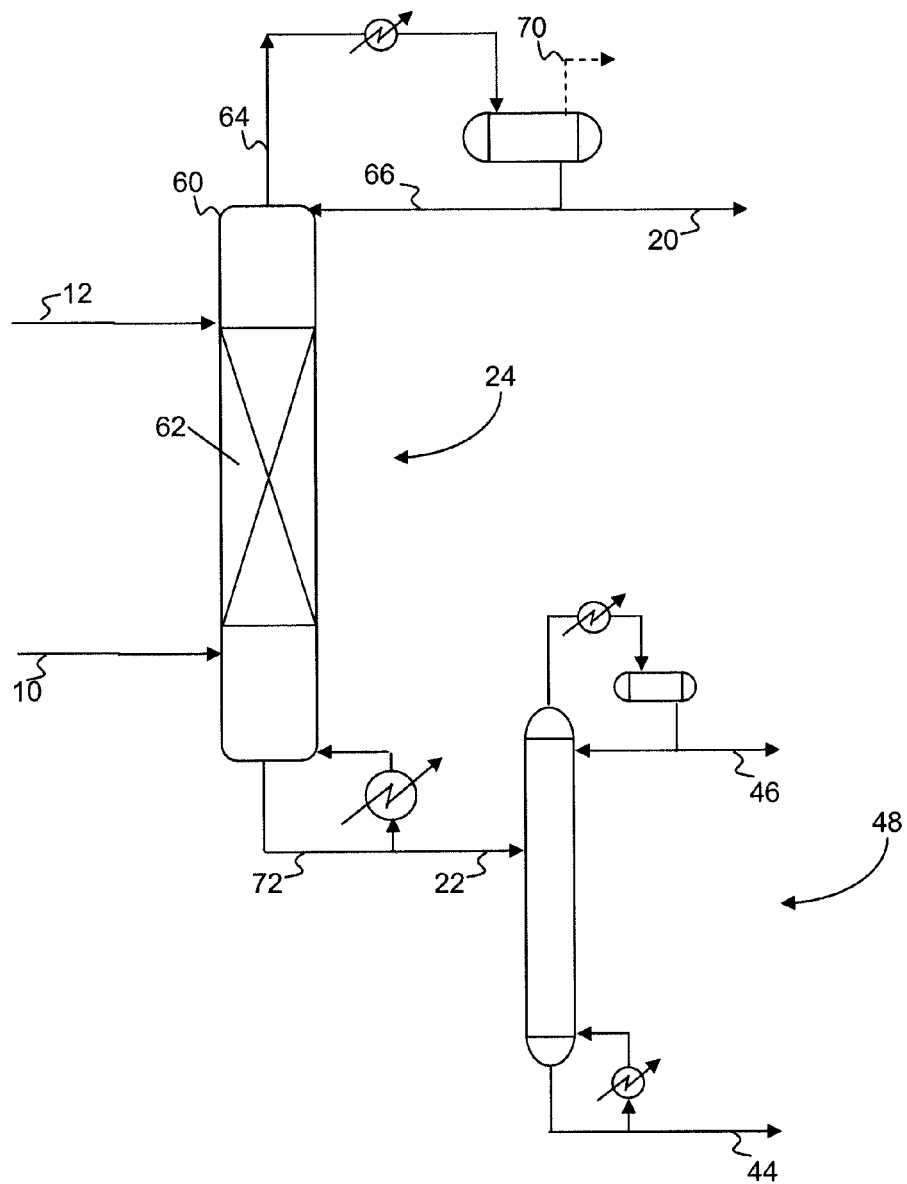
FIG. 2 is a simplified process flow diagram of a process for the conversion of alcohols to olefins according to embodiments disclosed herein.

Referring now to FIG. 2, a simplified process flow diagram of processes for the conversion of alcohols to olefins according to embodiments disclosed herein is illustrated, where like numerals represent like parts. In this embodiment, the process streams 10, 12 are fed to a reaction/separation zone 24 including a catalytic distillation reactor system 60 (i.e., integrating reaction zone 14 and separation zone 18) having at least one reaction zone 62 containing an esterification catalyst, above and/or below of which may be traditional distillation stages (not shown) for separating the reactants and products. Concurrently in catalytic distillation reactor system 60, i) the olefin and organic acid may be contacted in the presence of the esterification catalyst to form a reaction product comprising water and ester, and ii) the resulting reaction products, any unreacted alcohol, any unreacted organic acid, and any inert feed components, such as water fed along with the alcohol, may be separated.

As illustrated in FIG. 2, the flow of organic acid and alcohol are countercurrent through distillation reaction zone 14. Alcohol may be fed to the column below reaction zone 62, distill upward within the column and into contact with the catalyst. Organic acid may be fed to the column above reaction zone 62, distilling downward within the column and into contact with the catalyst. The flow of alcohol and organic acid may be reversed, depending upon the relative boiling points of the components.

Water that may be contained in the alcohol and/or organic acid fed to the column as well as that produced during formation of the ester product, along with any unreacted alcohol, may be recovered from catalytic distillation reactor system 60 as an overheads vapor fraction 64, which may be at least partially or totally condensed and recovered. As the overheads fraction condenses, immiscibility between particular alcohols and water exist such that the water can be phased out as a heavy liquid phase. In the condenser, two liquid phases may be present and the heavy aqueous phase is rejected from the process (primarily water) as aqueous fraction 20. The lighter liquid phase may be recycled to column 60 as reflux via flow line 66, and a portion may be recovered as aqueous fraction 20. Any uncondensed materials, such as light reaction byproducts or impurities in the feed, when present, may be recovered via vent 70, if necessary.

The ester reaction product and any unreacted organic acid may traverse downward through column 60 and be recovered as a bottoms fraction via flow line 72. A portion of the bottoms fraction may be heated and used to provide reboil vapor traffic to the column, and a portion of the bottoms fraction may be forwarded as ester fraction 22 (reporting as bottoms). The ester fraction 22, or a portion thereof following alcohol recovery, may then be fed to separation/reaction zone 48 for conversion of the ester to the desired olefin. As illustrated in FIG. 2, separation/reaction zone 48 includes a non-catalytic distillation reactor system operating at a bottoms temperature sufficient to decompose the ester to the desired products, organic acid and olefin. By feeding ester via stream 22, decomposition of the ester results in separation zone 48 and the resulting olefin product is concurrently separated in the non-catalytic distillation reactor system to recover an organic acid fraction 44 as bottoms and an olefin fraction 46 as overheads. This configuration is particularly useful for the esterification of n-butanol with acetic acid and the resulting production of normal butylenes.

A reaction-separation train similar to that used in FIG. 2 may likewise be used to convert other alcohols to olefins according to embodiments disclosed herein, whereby the ester reports as an overhead fraction in the first catalytic esterification step. For example, referring to FIG. 3, an ethanol/water mixture and formic acid may be fed via flow lines 10 and 12, respectively, to catalytic distillation reactor system 60. Reaction over an esterification catalyst in bed 62 may produce ethyl formate, recovered as an overheads product via flow line 64, with water being recovered as a bottoms product via flow line 72. The ethyl formate recovered may then be processed similar to that as described above with respect to FIGS. 1 and 2 to return an essentially pure ethylene product.

Figure 3:
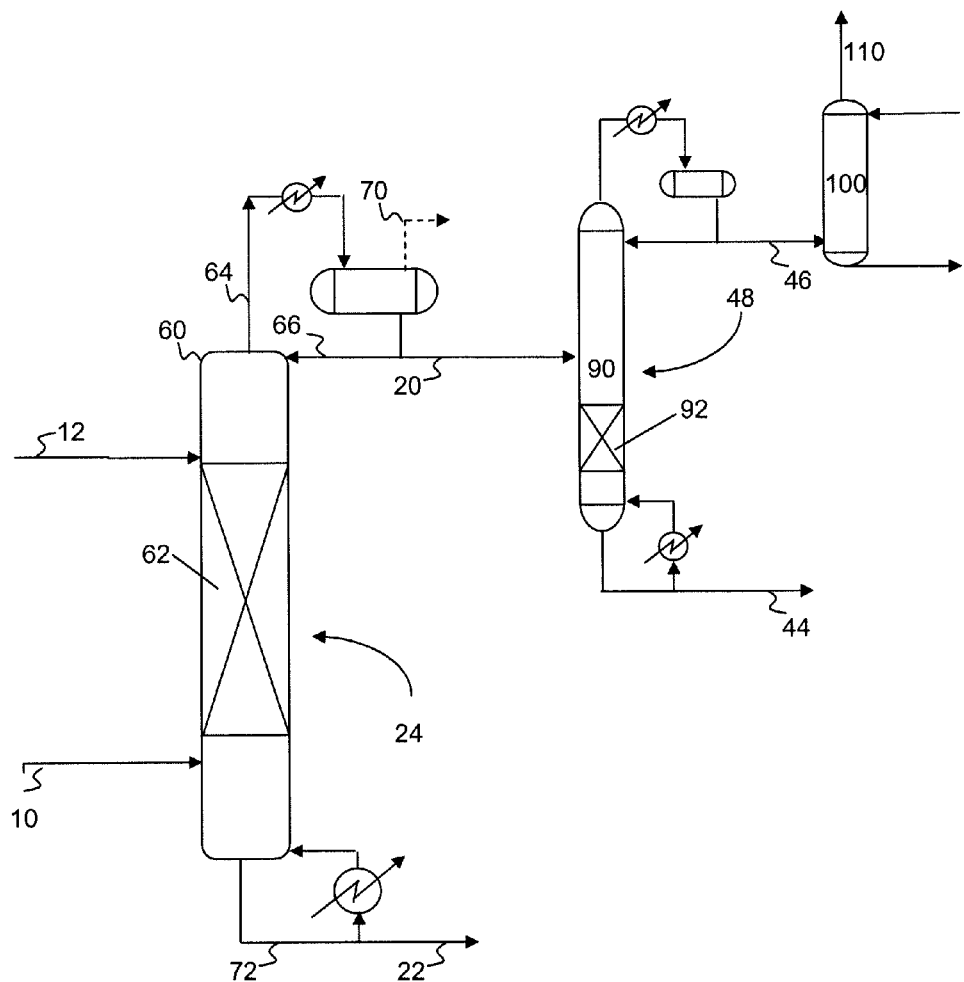
FIG. 3 is a simplified process flow diagram of a process for the conversion of alcohols to olefins according to embodiments disclosed herein.

As illustrated in FIG. 3, reaction/separation zone 48 may include a catalytic distillation reactor system 90 operated at a temperature profile sufficient to decompose the ester to olefins and carboxylic acid with a decomposition catalyst in reaction zone 92. Concurrently, separation of the products takes place. A water wash column 100 may be used to remove any alcohols fed to the decomposition section and remove trace carboxylic acid. The ethylene product recovered via flow line 110 may then be incorporated into various end products as known in the art.

In this particular case, when applied to formic acid reacting with ethanol to produce ethyl formate, the system is azeotropic, containing an ethanol/ethylformate azeotrope overhead and a water/formic acid azeotrope at the bottom. For the overhead, the azeotropic conditions is low in reactant ethanol, with the azeotropic composition, depending on operating conditions, nominally around 10%-4% mole fraction ethanol present. Being dilute in ethanol reactant, this feed can go direct to the thermal or catalytic degradation step (back cracking), and the remaining azeotropic ethanol recovered using a water wash, to remove ethanol from the desired ethylene product. For this system the reaction equilibrium constant is such that given a high enough activity catalyst to allow for esterification in the presence of the azeotropic amount of water, the azeotrope can be overcome to provide a bottoms that is a highly concentrated water stream when a catalytic distillation column is used. If not reacted away within the catalytic distillation column, the azeotropic composition of formic acid with water is around 40 mol % water in formic acid.

Figure 4:
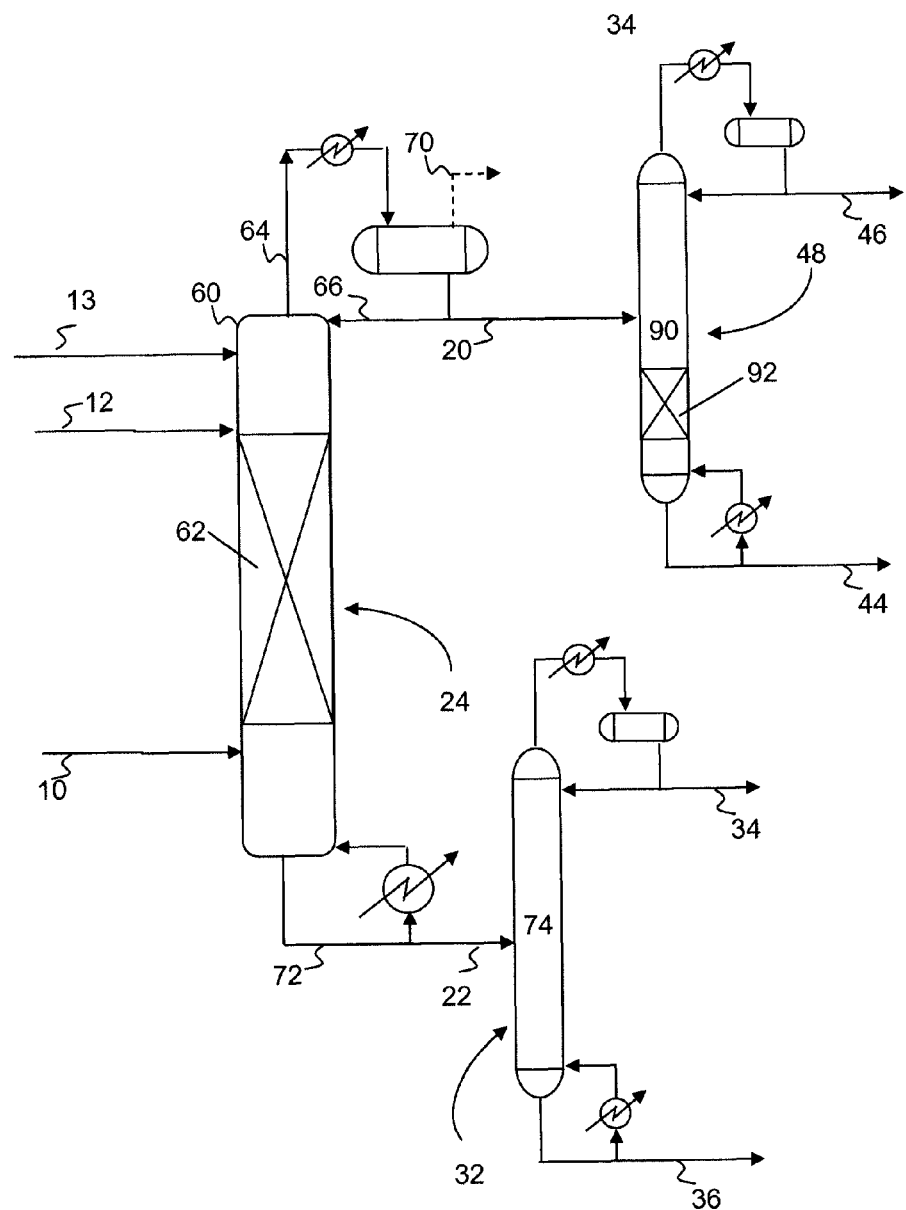
FIG. 4 is a simplified process flow diagram of a process for the conversion of alcohols to olefins according to embodiments disclosed herein.

Referring now to FIG. 4, a simplified process flow diagram of processes for the conversion of alcohols to olefins according to embodiments disclosed herein is illustrated, where like numerals represent like parts. In this embodiment, the process streams 10, 12, such as acetic acid and isobutanol, are fed to a reaction/separation zone 24. Prior to this reaction/separation zone, a fixed bed reactor may be utilized for a first treatment of streams 10 and 12. A fixed bed reactor (not shown) may contain one or more catalyst beds containing an esterification catalyst for at least partial conversion of the alcohol and organic acid to ester and water. For example, acetic acid and isobutanol may be reacted to form isobutyl acetate. The effluent from fixed bed reactor is then fed to catalytic distillation reactor system 60 for further conversion of the alcohol and organic acid to ester (further conversion of isobutanol and acetic acid to isobutyl acetate).

Catalytic distillation reactor system 60 may include at least one reaction zone 62 containing an esterification catalyst, above and/or below of which may be traditional distillation stages (not shown) for separating the reactants and products. Concurrently in catalytic distillation reactor system 60: i) the alcohol and organic acid may be contacted in the presence of the esterification catalyst to form a reaction product comprising water and ester, and ii) the resulting reaction products, any unreacted alcohol, any unreacted organic acid, and any inert feed components, such as water fed along with the alcohol (isobutanol), may be separated.

In the process as illustrated in FIG. 4, isobutanol may be reacted with acetic acid to produce water and isobutyl ester. There are several binary azeotropes, including isobutyl acetate/water azeotrope (occurring at approximately 84% wt isobuyl acetate), isobutanol/water azeotrope (occurring at approximately 67% wt isobutanol), and isobutyl acetate/isobutanol azeotrope (occurring at approximately 55% wt isobutanol). As such, a ternary azeotrope exists between isobutanol, isobutyl acetate, and water. Solutions for resolving this azeotrope exist to those skilled in the art, such as those identified in U.S. Pat. No. 4,724,049. Utilizing an extractive agent injection within the catalytic distillation column will heavy up the aqueous fraction within the distillation column and increase the relative volatility of isobutyl acetate. The catalytic distillation can incorporate a heavy extractive agent to break the azeotrope within the rectification section as a means to recover the product isobutyl acetate and isobutanol within the catalytic distillation column overheads section. When incorporating an extractive agent, water will be removed as bottoms along with the acetic acid.

In the case of no or low extractive agent use, some water that may be contained in the alcohol and/or organic acid fed to the column as well as that produced during formation of the ester product, may accompany the ester product as overhead azeotropic material. This water may be recovered from catalytic distillation reactor system 60 as an overheads vapor fraction 64, which may be at least partially or totally condensed and recovered, where a fraction of the condensate may be recycled to column 60 as reflux via flow line 66, and a portion may be recovered as aqueous fraction 20. Any uncondensed materials, such as light reaction byproducts or impurities in the feed, when present, may be recovered via vent 70.

When an extractive agent injection is used, depicted as stream 13, the water will report as bottoms along with the heavy extractive agent. The water and extractive agent traverse downward through column 60 and are recovered as a bottoms fraction via flow line 72. A portion of the bottoms fraction may be heated and used to provide reboil vapor traffic to the column, and a portion of the bottoms fraction may be forwarded as stream 22 to separation zone 74 for further processing. In distillation column 74, the water is separated from the extractive agent, with the water being taken overhead as stream 34.

The ester reaction product, such as isobutyl acetate, recovered as an overheads via flow line 20 may then be fed to reaction/separation zone 48 including a catalytic distillation reactor system 90 including one or more reaction zones 92 containing a decomposition catalyst. Catalytic distillation reactor system 90 is operated at a temperature profile sufficient to decompose the ester, such as isobutyl acetate, to the desired products, organic acid and olefin, such as acetic acid and isobutylene, when contacted with decomposition catalyst in reaction zone 92. The decomposition reaction product may concurrently be separated in catalytic distillation reactor system 90 to recover an organic acid fraction 44 and an olefin fraction 46.

In other embodiments, although not illustrated, reaction/separation zone 48 may include a catalytic or non-catalytic flow reactor (e.g., a heater, a fixed bed reactor, etc.) for at least partial decomposition of the ester, followed by a catalytic distillation reactor system 90 or a non-catalytic distillation reactor system 76, for additional decomposition and separation of the decomposition reaction products.

As illustrated and described with respect to FIG. 1-4, the ester fraction (22 or 36, depending upon impurity content) may be fed to a distillation column or catalytic distillation reactor system at a point above the thermal or catalytic reaction zones, distilling downward into the reaction zone and decomposing into the olefin, which distills upward within the column, and organic acid, which continues to distill downward within the column. A catalytic reaction zone (not illustrated) may additionally be placed above the ester feed to react the olefin(s) to form dimer or trimer products. For example, decomposition of isobutyl acetate may form isobutylene and acetic acid. The isobutylene may distill upward within the column, contacting an oligomerization catalyst to produce isooctene, for example, which, having a boiling point sufficiently different from acetic acid, may be recovered as an overheads product.

As described above, processes disclosed herein provide for the conversion of light alcohols to olefins. Conversion of light alcohols to olefins according to embodiments disclosed herein may proceed via esterification of the alcohol with an organic acid to form an ester, followed by degradation of the ester to form an organic acid and an olefin. For example, isobutanol may initially be reacted with acetic acid to form isobutyl acetate, a C6 ester. The isobutyl acetate may subsequently be thermally or catalytically degraded (cracked) to produce acetic acid and isobutylene.

Producing olefins from light alcohols in this manner may advantageously reduce or eliminate the need for high activity catalysts, severe processing conditions, and high recycle rates, as are typically required for dehydration of alcohols such as isobutanol and isopentanol. As such, processes disclosed herein provide for the conversion of various alcohols and bio-alcohols, including mixtures of bio-alcohols, to useful petrochemical compounds, including various olefins, including ethylene, propylene, isobutylene, and isoamylenes, and alternatively gasoline blend components, such as olefin dimers or trimers of the produced olefins.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for the conversion of an alcohol to an olefin, the process comprising:
    contacting at least one C4 to C5 alcohol with an organic acid in the presence of an esterification catalyst to convert at least a portion of the at least one C4 to C5 alcohol and the organic acid to an ester;
    and one of:
        catalytically degrading the ester, at a temperature in the range of 93° C. to 260° C., to form the organic acid and an olefin, the catalyst comprising one or more of metal-treated zeolites, acid-treated clays, and silica-alumina catalysts; and thermally degrading the ester, at a temperature in the range of 37° C. to 438° C., to form the organic acid and an olefin comprising isobutylene;

wherein the steps of degrading the ester and separating the degradation product occur concurrently in a distillation reactor system.

2. A process for the conversion of an alcohol to an olefin, the process comprising:

feeding at least one C4 to C5 alcohol with an organic acid to a catalytic distillation reactor system having at least one reaction zone containing an esterification catalyst;

concurrently in the catalytic distillation reactor system:

contacting the at least one C4 to C5 alcohol with the organic acid in the presence of the esterification catalyst to convert at least a portion of the at least one C4 to C5 alcohol and the organic acid to an ester and water; separating the water, ester, any unreacted organic acid, and any unreacted C4 to C5 alcohol;

recovering a first fraction from the catalytic distillation reactor system comprising water;

recovering a second fraction from the catalytic distillation reactor system comprising the ester;

and one of:

catalytically degrading the ester, at a temperature in the range of 93° C. to 260° C., to form the organic acid and an olefin, the catalyst comprising one or more of metal-treated zeolites, acid-treated clays, and silica-alumina catalysts;

and thermally degrading the ester in the second fraction, at a temperature in the range of 37° C. to 438° C., to form a degradation product comprising the organic acid and an olefin comprising isobutylene; and separating the degradation product to recover a third fraction comprising the organic acid and any unreacted ester and a fourth fraction comprising the olefin;

wherein the degrading the ester and the separating the degradation products is conducted concurrently in a distillation reactor system.

3. The process of claim 2, wherein the first fraction comprises water and unreacted alcohol and the second fraction comprises ester and unreacted organic acid.

4. The process of claim 3, further comprising at least one of:

separating the first fraction to recover an aqueous fraction comprising the water and an alcohol fraction comprising the unreacted alcohol;

separating the second fraction to recover an acid fraction comprising the unreacted organic acid and an ester fraction comprising the ester;

recycling at least a portion of the third fraction to the one of catalytically and thermally degrading;

recycling at least a portion of the third fraction to the catalytic distillation reactor system;

recycling at least a portion of the alcohol fraction to the catalytic distillation reactor system; and recycling at least a portion of the acid fraction to the catalytic distillation reactor system.

5. The process of claim 2, wherein the first fraction comprises water and unreacted organic acid and the second fraction comprises ester and unreacted alcohol.

6. The process of claim 5, further comprising at least one of:

separating the first fraction to recover an aqueous fraction comprising the water and an acid fraction comprising the unreacted organic acid;

separating the second fraction to recover an alcohol fraction comprising the unreacted alcohol and an ester fraction comprising the ester;

recycling at least a portion of the third fraction to the one of catalytically and thermally degrading;

recycling at least a portion of the third fraction to the catalytic distillation reactor system;

recycling at least a portion of the acid fraction to the catalytic distillation reactor system; and recycling at least a portion of the alcohol fraction to the catalytic distillation reactor system.

7. The process of claim 2, wherein the fourth fraction further comprises organic acid, the process further comprising water washing the fourth fraction, partitioning at least a portion of the organic acid into the water and recovering an olefin fraction having a reduced organic acid content as compared to the fourth fraction.

8. The process of claim 2, wherein the at least one C4 to C5 alcohol comprises isobutanol.

9. The process of claim 8, wherein the isobutanol is obtained from a fermentation process.

10. The process of claim 2, wherein the organic acid comprises at least one of acetic acid, formic acid, succinic acid, and lactic acid.

11. The process of claim 2, wherein the organic acid is acetic acid and the at least one C4 to C5 alcohol comprises at least one of n-butanol, 2-butanol, and isobutanol.

12. A process for the conversion of an alcohol to an olefin, the process comprising:

feeding at least one C4 to C5 alcohol with an organic acid to a first reaction zone containing an esterification catalyst;

contacting the at least one C4 to C5 alcohol with the organic acid in the presence of the esterification catalyst to convert at least a portion of the at least one C4 to C5 alcohol and the organic acid to an ester and water;

recovering a reactor effluent from the first reaction zone comprising water, ester, unreacted organic acid, and unreacted C4 to C5 alcohol;

feeding the reactor effluent from the first reaction zone to a catalytic distillation reactor system having at least one reaction zone containing an esterification catalyst;

concurrently in the catalytic distillation reactor system:

contacting the unreacted C4 to C5 alcohol with the unreacted organic acid in the presence of the esterification catalyst to convert at least a portion of the at least one C4 to C5 alcohol and the organic acid to an ester and water;

separating the water, ester, any unreacted organic acid, and any unreacted C4 to C5 alcohol;

recovering a first fraction from the catalytic distillation reactor system comprising water;

recovering a second fraction from the catalytic distillation reactor system comprising the ester;

and one of:

catalytically degrading the ester, at a temperature in the range of 93° C. to 260° C., to form the organic acid and an olefin, the catalyst comprising one or more of metal-treated zeolites, acid-treated clays, and silica-alumina catalysts; and thermally degrading the ester in the second fraction, at a temperature in the range of 37° C. to 438° C., to form a degradation product comprising the organic acid and an olefin comprising isobutylene; and separating the degradation product to recover a third fraction comprising the organic acid and any unreacted ester and a fourth fraction comprising the olefin comprising isobutylene;

wherein the steps of degrading the ester and separating the degradation product occur concurrently in a distillation reactor system.

13. The process of claim 12, further comprising feeding the second fraction to a reaction zone for one of catalytically and thermally degrading at least a portion of the ester prior to the concurrent degrading and separating.

14. The process of claim 12, wherein the catalytic distillation reactor system further comprises an oligomerization catalyst for converting at least a portion of the olefin comprising isobutylene to dimer.

15. The process of claim 12, wherein the first fraction comprises water and unreacted alcohol and the second fraction comprises ester and unreacted organic acid.

16. The process of claim 15, further comprising at least one of:
separating the first fraction to recover an aqueous fraction comprising the water and an alcohol fraction comprising the unreacted alcohol;
separating the second fraction to recover an acid fraction comprising the unreacted organic acid and an ester fraction comprising the ester;
recycling at least a portion of the third fraction to the one of catalytically and thermally degrading;
recycling at least a portion of the third fraction to the catalytic distillation reactor system;
recycling at least a portion of the alcohol fraction to the catalytic distillation reactor system; and
recycling at least a portion of the acid fraction to the catalytic distillation reactor system.

17. The process of claim 12, wherein the first fraction comprises water and unreacted organic acid and the second fraction comprises ester and unreacted alcohol.

18. The process of claim 17, further comprising at least one of separating the first fraction to recover an aqueous fraction comprising the water and an acid fraction comprising the unreacted organic acid;
separating the second fraction to recover an alcohol fraction comprising the unreacted alcohol and an ester fraction comprising the ester;
recycling at least a portion of the third fraction to the one of catalytically and thermally degrading;
recycling at least a portion of the third fraction to the catalytic distillation reactor system;
recycling at least a portion of the acid fraction to the catalytic distillation reactor system; and
recycling at least a portion of the alcohol fraction to the catalytic distillation reactor system.

19. The process of claim 12, wherein the fourth fraction further comprises organic acid, the process further comprising water washing the fourth fraction, partitioning at least a portion of the organic acid into the water and recovering an olefin fraction having a reduced organic acid content as compared to the fourth fraction.

20. The process of claim 12, wherein the at least one C4 to C5 alcohol comprises isobutanol.

21. The process of claim 20, wherein the isobutanol is obtained from a fermentation process.

22. The process of claim 12, wherein the organic acid comprises at least one of acetic acid, formic acid, succinic acid, and lactic acid.

23. The process of claim 12, wherein the organic acid is acetic acid and the at least one C4 to C5 alcohol comprises at least one of n-butanol, 2-butanol, and isobutanol.

* * * * *